US00PP28273P3

(12) United States Plant Patent
Fraser

(10) Patent No.: US PP28,273 P3
(45) Date of Patent: Aug. 15, 2017

(54) ***COPROSMA* PLANT NAMED 'IGNITE'**

(50) Latin Name: *Coprosma repens*
Varietal Denomination: Ignite

(71) Applicant: Peter Fraser, Kihikihi (NZ)

(72) Inventor: Peter Fraser, Kihikihi (NZ)

( * ) Notice: Subject to any disclaimer, the term of this patent is extended or adjusted under 35 U.S.C. 154(b) by 125 days.

(21) Appl. No.: 14/545,556

(22) Filed: May 20, 2015

(65) Prior Publication Data

US 2016/0345483 P1 Nov. 24, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Coprosma repens* named 'IGNITE' is disclosed, characterized by Greyed-Purple foliage with a red and greyed-purple margin and glossy, ovate leaves. Plant habit is dense and round. The new cultivar is a *Coprosma repens*, typically suited for ornamental container and landscape use.

2 Drawing Sheets

Latin name of the genus and species: *Coprosma repens*.
Variety denomination: 'IGNITE'.

BACKGROUND OF THE INVENTION

The new cultivar is the result of chance discovery in a commercial nursery in Waikato, New Zealand. The inventor, Peter Fraser, discovered the new variety as a single branch, naturally occurring mutation growing in a planting of the parent variety *Coprosma repens* 'Evening Glow', unpatented. The discovery was made in the April of 2009. First propagation was performed by vegetative cuttings during the Summer of 2009 in Waikato, New Zealand. Multiple additional generations have been propagated. This subsequent propagation has shown the unique features of this cultivar are stable and reproduced true to type.

The inventor has filed for Plant Breeder's Rights in Australia, with a grant date of Sep. 12, 2012, application number 2012/173. Additionally, the inventor has filed for Plant Breeder's Rights in New Zealand, receiving grant number 30979 Apr. 29, 2014. The inventor filed these applications before any sales of 'Ignite' began. First sale of 'Ignite' occurred within one year of the filing of this US application.

SUMMARY OF THE INVENTION

The cultivar 'IGNITE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IGNITE'. These characteristics in combination distinguish 'IGNITE' as a new and distinct *Coprosma* cultivar:

1. Vibrant foliage with a Greyed-Purple center and Red and Greyed-Purple margin.
2. Ovate foliage shape.
3. Dense plant growth.

PARENTAL COMPARISON

Plants of the new cultivar 'IGNITE' are similar to the parent, 'Evening Glow' in most horticultural characteristics. However, 'IGNITE' differs in foliage color. Foliage of the new variety is distinctly greyed-purple in the center, with a red and purple margin. Foliage of the parent variety is light pink, green and yellow. Plants of the new variety grow more densely than plants of the parent variety.

COMMERCIAL COMPARISON

Plants of the new cultivar 'IGNITE' can be compared to the patented commercial variety *Coprosma* 'Inferno' U.S. Plant Pat. No. 23,260. Plants of 'IGNITE' are similar to 'Inferno' in most horticultural characteristics, however, 'IGNITE' has ovate compared to oblong foliage. Foliage of the new variety is distinctly greyed-purple in the center, with a red and purple margin. Foliage of this comparator is Greyed-Purple with Green. Additionally, plants of the new variety are denser than plants of this comparator.

BRIEF DESCRIPTION OF THE PHOTOGRAPHS

Figure 1:
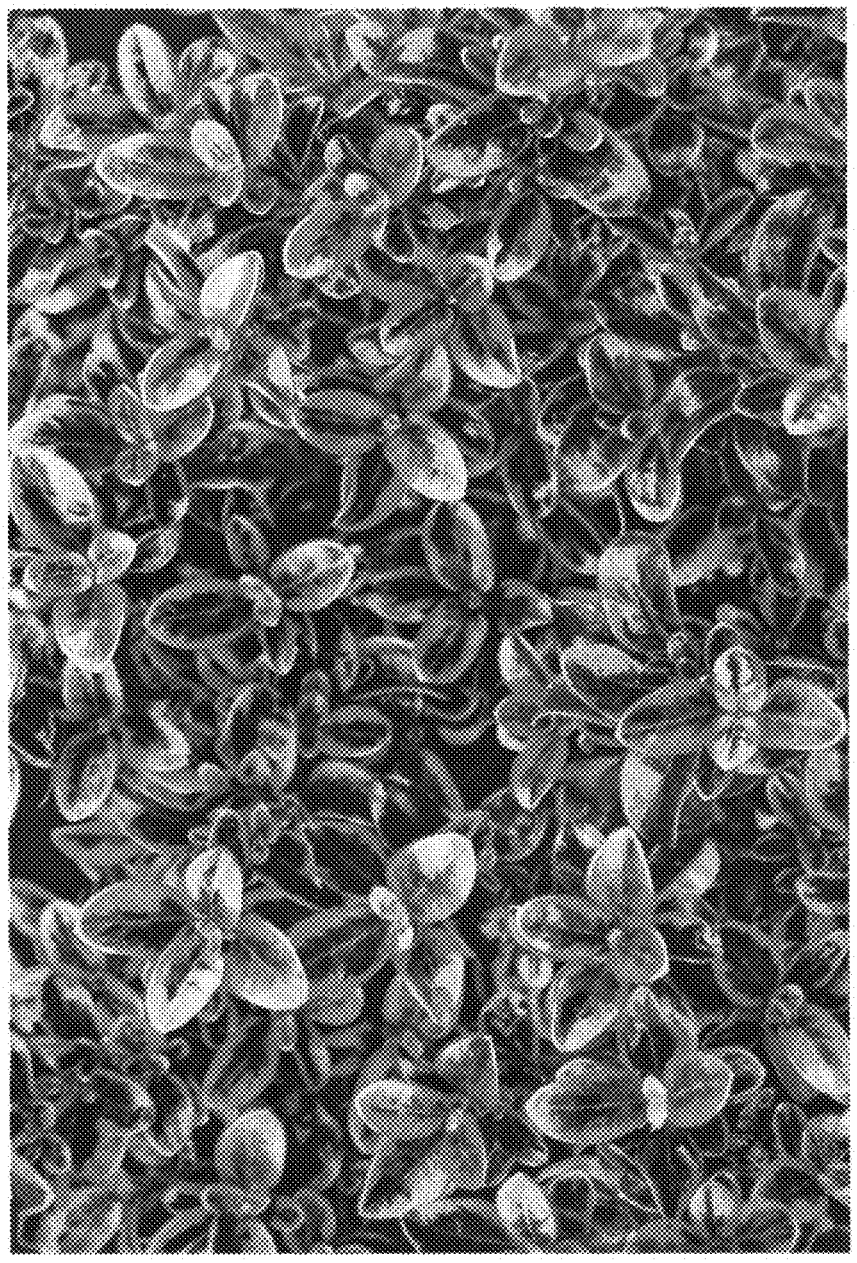

The accompanying photograph in FIG. 1 illustrates in full color typical foliage of the new variety.

Figure 2:
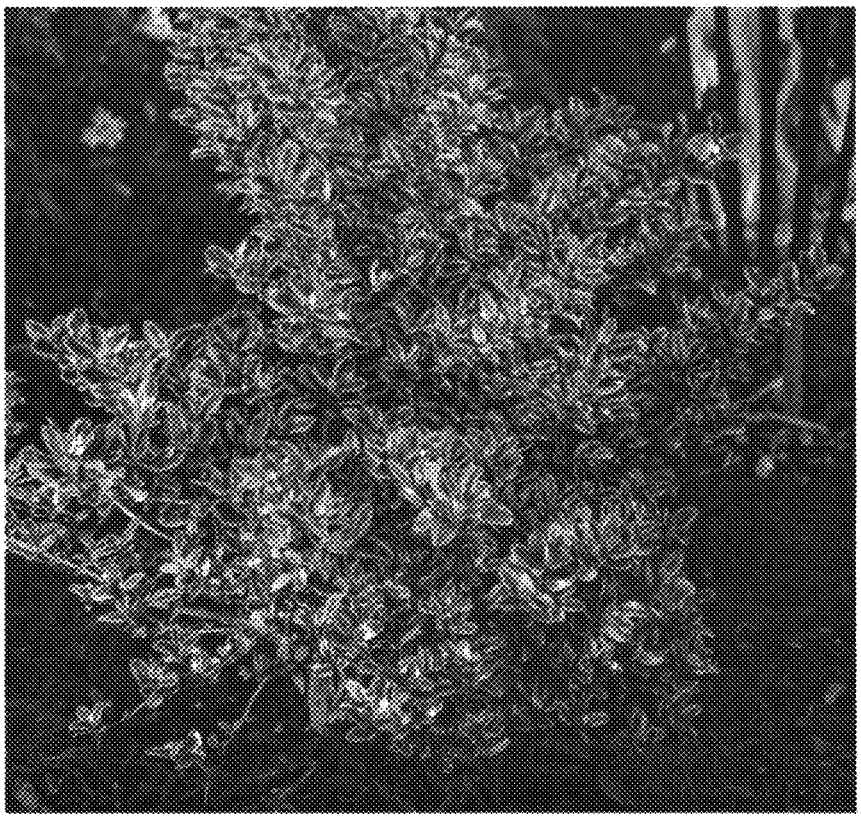

FIG. 2 illustrates in full color a typical plant of 'IGNITE' grown outdoors in Waikato, New Zealand. This plant is approximately 18 months.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'IGNITE' plants grown outdoors in Waikato, New Zealand. Temperatures ranged from approximately 0° C. to 10° C. at night to 2° C. to 18° C. during the day. No artificial light, photoperiodic treatments or chemical treatments were given to the plants. Measurements and numerical values represent averages of typical plant types.

Botanical classification: *Coprosma repens* 'IGNITE'.

Age of the plant described: Approximately 200 days from a rooted cutting.

PROPAGATION

Time to initiate roots: Approximately 18 days at approximately 20° C.

Root description: Fine, densely branched, non-fibrous, non-fleshy.

PLANT

Growth habit: Rounded, compact bush.

Height: Approximately 150 cm.

Plant spread: Approximately 150 cm.

Stem diameter: Approximately 0.3 cm.

Quantity of lateral branches: Approximately 20 per 200 mm length.

Average lateral branch length: Approximately 4.0 cm.

Color of lateral branches:

*Mature*.—Near RHS Green 138A.

*Young branches*.—Near RHS Greyed-Green 195B.

Aspect and angle: Straight, occurring at approx. 45 degree angle from stem.

Strength of lateral branches: Moderate.

Internode length: Approximately 1.0 cm.

FOLIAGE

Leaf:

*Arrangement*.—Opposite, sessile.

*Average length*.—Approximately 30 mm.

*Average width*.—Approximately 20 mm.

*Shape of blade*.—Ovate.

*Apex*.—Mucronate.

*Base*.—Blunt.

*Attachment*.—Sessile.

*Margin*.—Entire.

*Texture of top surface*.—Smooth.

*Texture of bottom surface*.—Smooth.

*Appearance of top surface*.—Glossy.

*Appearance to bottom surface*.—Glossy.

*Leaf internode length*.—10 mm.

*Color*.—Young foliage upper side: Near RHS inner color 139A, outer edge 169A. Young foliage under side: Near RHS inner color 144B, outer edge 10B. Mature foliage upper side: Near RHS inner color 187B, mid color 42B, outer edge 187B, in Winter months. Mature foliage under side: Near RHS inner color 138B, outer edge 63A.

*Venation*.—Type: Pinnate. Venation color upper side: Indistinguishable from leaf blade. Venation color under side: Indistinguishable from leaf blade.

FLOWER

Not observed to date.

OTHER CHARACTERISTICS

Seeds and fruits: Not observed to date.

Disease/pest resistance: Neither resistance nor susceptibility to normal diseases and pests of *Coprosma* has been observed.

Temperature tolerance: The new variety tolerates low temperatures to approximately 5° C. and has been observed to tolerate high temperatures to at least 30° C.

What is claimed is:

1. A new and distinct cultivar of *Coprosma repens* plant named 'IGNITE' as herein illustrated and described.

* * * * *